United States Patent [19]

Nemet-Mavrodin

[11] Patent Number: 5,059,735

[45] Date of Patent: Oct. 22, 1991

[54] PROCESS FOR THE PRODUCTION OF LIGHT OLEFINS FROM $C_5+$ HYDROCARBONS

[75] Inventor: Margaret Nemet-Mavrodin, Cherry Hill, N.J.

[73] Assignee: Mobil Oil Corp., Fairfax, Va.

[21] Appl. No.: 643,706

[22] Filed: Jan. 22, 1991

Related U.S. Application Data

[63] Continuation of Ser. No. 347,308, May 4, 1989, abandoned.

[51] Int. Cl.$^5$ .......................... C07C 5/393; C07C 5/32
[52] U.S. Cl. .................................. 585/418; 585/407; 585/415; 585/419; 585/651; 585/653
[58] Field of Search ............... 585/407, 415, 419, 651, 585/653, 648, 418

[56] References Cited

U.S. PATENT DOCUMENTS

| | | | |
|---|---|---|---|
| 3,756,942 | 9/1973 | Cattanach | 585/407 |
| 3,759,821 | 9/1973 | Brennan et al. | 208/93 |
| 3,760,024 | 9/1973 | Cattanach | 585/415 |
| 3,890,218 | 6/1975 | Morrison | 585/407 |
| 4,180,689 | 12/1979 | Davies et al. | 585/407 |
| 4,304,657 | 12/1981 | Miller | 585/415 |
| 4,547,616 | 10/1985 | Avidan et al. | 585/640 |
| 4,565,897 | 1/1986 | Gane et al. | 585/415 |
| 4,642,404 | 2/1987 | Shihabi | 585/415 |
| 4,720,602 | 1/1988 | Chu | 585/415 |
| 4,746,762 | 5/1988 | Avidan et al. | 585/415 |
| 4,754,100 | 6/1988 | Sorensen et al. | 585/708 |
| 4,766,264 | 8/1988 | Bennett et al. | 585/415 |
| 4,788,370 | 11/1988 | Chang et al. | 585/415 |
| 4,922,051 | 5/1990 | Nemet-Mavrodin | 585/407 |
| 4,982,033 | 1/1991 | Chu et al. | 585/407 |

FOREIGN PATENT DOCUMENTS

| | | | |
|---|---|---|---|
| 0036292 | 9/1981 | European Pat. Off. | 585/407 |
| 0222428 | 11/1985 | Japan | 585/407 |
| 215579A | 3/1987 | United Kingdom . | |

*Primary Examiner*—Asok Pal
*Attorney, Agent, or Firm*—Alexander J. McKillop; Charles J. Speciale; Robert B. Furr, Jr.

[57] ABSTRACT

The $C_2$-$C_4$ olefin yield is unexpectedly increased while coke and heavy aromatics production are decreased by the addition of a propane-rich supplemental feedstream in a process for catalytically upgrading $C_5$-$C_7$ paraffinic feedstreams. Further benefits include increased conversion of the $C_5$-$C_7$ paraffinic feedstream, decreased coke production and prolonged catalyst useful life. Udex raffinate is a particularly preferred feedstream.

18 Claims, No Drawings

PROCESS FOR THE PRODUCTION OF LIGHT OLEFINS FROM $C_5+$ HYDROCARBONS

This is a continuation of copending application Ser. No. 347,308, filed on May 4, 1989, now abandoned.

BACKGROUND OF THE INVENTION

This invention relates to the conversion of paraffins into more valuable olefinic and aromatic products. In particular, the invention relates to a process for increasing the yield of valuable $C_2-C_4$ olefins from the conversion of a stream rich in $C_5-C_9$ paraffins, cycloparaffins and olefins in the presence of a medium-pore zeolite catalyst having a relatively low acid activity.

Conversion of paraffinic feedstocks to more valuable aromatic and olefinic product streams is known. For example, U.S. Pat. No. 3,756,942 discloses a process for the preparation of aromatic compounds in high yields which involves contacting a particular feed consisting essentially of mixtures of paraffins and/or olefins, and/or naphthenes with a crystalline aluminosilicate, e.g. ZSM-5, under conditions of temperature and space velocity such that a significant portion of the feed is converted directly into aromatic compounds. U.S. Pat. No. 3,759,821 discloses a similar process for upgrading catalytically cracked gasoline. Finally, U.S. Pat. No. 3,760,024 teaches a process for the preparation of aromatic compounds which involves contacting a feed consisting essentially of $C_2-C_4$ paraffins and/or olefins with a crystalline aluminosilicate, e.g. ZSM-5. The above references are incorporated herein by reference and are cited in particular for descriptions of useful feedstocks and process conditions.

Conversion has been found to be enhanced in fluidized bed processes by maintaining the fluidized bed reaction zone in a turbulent regime. For example, U.S. Pat. No. 4,547,616 to Avidan et al. teaches a process for the conversion of oxygenates to lower olefins in a turbulent fluidized bed of catalyst. U.S. Pat. No. 4,746,762 to Avidan et al. teaches a process for upgrading light olefins in a turbulent fluidized catalyst bed reactor. The Avidan et al. references are incorporated herein by reference and are cited in particular for the details of fluidized-bed operating variables.

The paraffin conversion processes mentioned above evolve product slates containing varying amounts of desired olefins and aromatics. The most economically attractive of these compounds are light olefins such as ethylene, propylene, and butylene, $C_5+$ gasoline rich in aromatics and hydrogen. Previous processes have sought to maximize $C_5+$ aromatics yield. Recent strengthening in the light olefin market has focused attention on increasing light olefins yield, particularly in petrochemical plants where light olefins are a basic building block for a broad spectrum of end products including thermoplastics. By way of contrast, $C_1-C_3$ paraffins (i.e. methane, ethane and propane) particularly in admixture, are less valuable chemicals which are generally used for fuel.

From the foregoing, it can therefore well be seen that it would be highly desirable to shift selectivity in a process for upgrading paraffinic feedstreams toward more valuable products including $C_6-C_8$ aromatics and $C_2-C_4$ olefins. Further, it would be particularly beneficial to react a relatively low value stream such as propane to enhance light olefin production in a paraffin upgrading process. Previous processes have employed supplemental feedstreams to control product selectivity.

The addition of selected supplemental feedstreams has been shown to effect desirable shifts in product selectivities. For example, European Patent Application EP 215-579A teaches a process in which the aromatics selectivity of an ethylene aromatization process is enhanced by the addition of at least 5 wt. % methane to the feedstock.

U.S. Pat. No. 4,565,897 to Gane et al discloses a process for producing aromatics from a feedstock comprising $C_3/C_4$ hydrocarbons mixed with ethane. The feedstock preferably contains at least 70 wt. % of $C_3/C_4$ hydrocarbons. The presence of ethane in the mixed feed was found to improve conversion selectivity for aromatics.

U.S. Pat. No. 4,754,100 to Sorensen et al described a process for the production of butanes and $C_5+$ aliphatic hydrocarbons from propane in which unexpectedly high selectivity to n-butane, isobutane, pentanes and $C_6+$ aliphatics is attained by the addition of a controlled amount of mono-olefin to the catalytic reaction zone.

The previous processing schemes for upgrading aliphatic, particularly paraffinic feedstreams have not addressed methods for increasing selectivity both to aromatics and to light olefins.

Propane, a naturally occurring material and a by-product of many petroleum refining processes, has a low economic value and is often burned as a fuel gas or used as a component in liquefied petroleum gas (LPG). Thus, a process which improves the selectivity or a paraffin upgrading process to yield more valuable products by co-feeding a relatively low value feedstock such as propane would provide a significant economic benefit.

SUMMARY OF THE INVENTION

In accordance with the present invention, it has been found that the selectivity of a paraffin upgrading process catalyzed by a low-acidity medium-pore zeolite may be beneficially shifted to favor $C_2-C_4$ olefins and $C_6+$ aromatics by co-feeding a supplemental feedstream comprising more than about 50 wt % propane. Surprisingly, rather than to decrease the extent of reaction of the primary paraffinic feedsteam, the addition of a secondary propane-rich feedstream appears to increase conversion of the primary feedstream. The beneficial increase in a light olefins yield results from a shift in selectivity and not merely from dehydrogenation of the secondary propane feedstream. This result is particularly unexpected as the lower residence time (higher space velocity) and lower primary paraffinic feedstream partial pressure would be exected to decrease the extent of conversion of the primary paraffinic feedstream.

The process of the invention further unexpectedly reduces coke yield and the catalyst aging rate.

The present invention provides a process for converting a paraffinic feedstream containing at least 85 weight percent $C_5-C_7$ paraffins comprising the steps of charging said paraffinic feedstream to a reaction zone containing a composite catalyst comprising a zeolite having a Constraint Index of between 1 and about 12 and Alpha Value of between 10 and 30 together with a feedstream containing at least 85 weight percent propane under conversion conditions including temperature of from about 400° C. to about 700° C., pressure of from about 0.1 atmosphere to about 60 atmospheres and weight hourly space velocity from about 0.1 to about 400; controlling the mass flowrate of said supplemental feedstream to maintain a weight ratio of $C_6$-$C_7$ paraffins to propane of between about 2:1 and 3:1; and recovering a product having more than 40 weight percent $C_2$-$C_4$ olefins and more than 10 weight percent $C_6+$ aromatics.

The invention further includes a method for improving the yield of $C_2$-$C_4$ olefins and decreasing the production of coke in a process for converting a paraffinic feedstream containing at least 85 weight percent $C_5$-$C_7$ paraffins comprising the steps of contacting said paraffinic feedstream and a second feedstream containing at least 85 weight percent propane with a composite catalyst containing a zeolite having a Constraint Index of between about 1 and about 12 and Alpha Value of between 5 and 30 under conversion conditions including temperature of from about 400° C. to about 700° C., pressure of from about 0.1 atmosphere to 60 atmospheres and weight hourly space velocity from about 0.1 to about 400; controlling the mass flowrate of said supplemental feedstream to maintain a weight ratio of $C_6$-$C_7$ paraffins to propane of between about 2:1 and 3:1; recovering a product having more than 40 weight percent $C_2$-$C_4$ olefins and more than 20 weight percent aromatics; and evolving less than 1.0 weight percent coke as a reaction byproduct.

DETAILED DESCRIPTION

The process of the present invention shifts the selectivity of a paraffin upgrading process to favor increased yield of valuable $C_2$-$C_4$ olefins by co-feeding a stream rich in propane.

Conversion Process

Hydrocarbon feedstocks which can be converted according to the present process include various refinery streams including coker gasoline, light FCC gasoline, $C_5$-$C_7$ fractions of straight run naphthas and pyrolysis gasoline, as well as raffinates from a hydrocarbon mixture which has had aromatics removed by a solvent extraction treatment. Examples of such solvent extraction treatments are described on pages 706-709 of the *Kirk-Othmer Encyclopedia of Chemical Technology*, Third Edition, Vol. 9, John Wiley and Sons, 1980. A particular hydrocarbon feedstock derived from such a solvent extraction treatment is a Udex raffinate. The paraffinic hydrocarbon feedstock suitable for use in the present process may comprise at least 75 percent by weight, e.g. at least 85 percent by weight, of paraffins having from 5 to 10 carbon atoms. The most preferred conversion process useful with the present invention is a paraffin aromatization process conducted under process conditions listed in Table 1. Operating pressures shown in Table 1 are based on aromatizable hydrocarbon partial pressures.

TABLE 1

| WHSV | Broad range: 0.3-300 hr$^{-1}$ |
|---|---|
| | Preferred range: 0.4-5 hr$^{-1}$ |
| OPERATING PRESSURE | Broad: 7-2170 kPa (1-315 psia) |
| | Preferred: 135-240 kPa (7-15 psia) |
| OPERATING TEMPERATURE | Broad: 540-820° C. (1000-1500° F.) |
| | Preferred: 560-630° C. (1050-1200° F.) |

Medium-Pore Zeolite Catalysts

The members of the class of zeolites useful in the process of the present invention have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as is set forth at length herein.

In a preferred embodiment, the catalyst is a zeolite having a Constraint Index of between about 1 and about 12. Examples of such zeolite catalysts include ZSM-5, ZSM-11, ZSM-12, ZSM-22, ZSM-23, ZSM-35 and ZSM-48.

Zeolite ZSM-5 and the conventional preparation thereof are described in U.S. Pat. No. 3,702,886, the disclosure of which is incorporated herein by reference. Other preparations for ZSM-5 are described in U.S. Pat. No. Re. 29,948 (highly siliceous ZSM-5); U.S. Pat. Nos. 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference.

The acid activity of the composite catalysts useful in the present invention are characterized by alpha values. When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec $^{-1}$). The Alpha Test is described in U.S. Pat. No. 3,354,078, in the *Journal of Catalysis,* Vol. 4, p. 527 (1965); Vol. 6, p. 278 (1966); and Vol. 61, p. 395 (1980), each incorporated herein by reference as to that description. The experimental conditions of the text used herein include a constant temperature of 538° C. and a variable flow rate as described in detail in the *Journal of Catalysis,* Vol. 61, p. 395.

In accordance with the present process, the present hydrocarbon feedstock is converted under sufficient conditions to convert at least 90 percent by weight (e.g. at least 93 percent by weight) of the aliphatics present into different hydrocarbons. These different hydrocarbons may comprise at least 90 percent by weight (e.g. at least 95 percent by weight) of the sum of $C_6$–$C_8$ aromatics, $C_2$–$C_4$ olefins, $C_{9}+$ aromatics and $C_1$–$C_3$ paraffins. The conversion of paraffins may be less than 100 percent, e.g. 99 percent by weight or less. Conversion of paraffins under extreme conditions may cause excessive coke formation on the catalyst and may result in the further conversion of $C_2$–$C_4$ olefins and $C_6$–$C_8$ aromatics into less desired products. The conversion products may include at least 68 percent by weight of the sum of $C_6$–$C_8$ aromatics plus $C_2$–$C_4$ olefins.

The catalyst suitable for use in accordance with the present invention may have an alpha value of from about 10 to about 20. This narrow range of alpha values may be achieved in a variety of ways. For example, the active zeolite portion of the catalyst could be blended with sufficient amounts of inert binder material. Thus, the ratio of binder to zeolite may be at least 70:30, preferably at least 95:5. Another way of achieving an alpha value within the desired range is to subject a more active catalyst, e.g. having an alpha value of at least 50 in the catalytically activated form, to sufficient deactivating conditions. Examples of such deactivating conditions include steaming the catalyst, coking the catalyst and high temperature calcination of the catalyst, e.g. at a temperature of greater than 700° C. It may also be possible to partially deactivate the catalyst by subjecting the catalyst to a sufficient amount of a suitable catalyst poison. Catalysts which have been deactivated in the course of organic compound conversions, particularly where the catalyst has been subjected to conditions of high temperature, coking and/or steaming, may be useful. Examples of such organic compound conversions include the present conversion of $C_5$–$C_{10}$ paraffins and the conversion of methanol into hydrocarbons.

It may also be possible to use zeolites which are intrinsically less active by virtue of having a high silica to alumina molar ratio of, e.g. greater than 100. However, since ZSM-5 may be more difficult to prepare at such higher silica to alumina ratios, particularly in the absence of an organic directing agent, it may be more desirable to use a more active form of ZSM-5, e.g. having a silica to alumina molar ratio of 100 or less. (Even though the alpha value of the activated form of such ZSM-5 may be rather high, the alpha value of the bound catalyst may be made much lower by one or more of the above-mentioned techniques. For example, ZSM-5 prepared from a reaction mixture not having an organic directing agent and having a framework silica to alumina molar ratio of about 70:1 or less may be bound with an inert binder at a binder: ZSM-5 weight ratio of 75:25, and the bound catalyst could be subjected to sufficient deactivating conditions involving high temperature calcination and/or steaming of the catalyst.

The catalyst suitable for use in accordance with the present invention may be free of intentionally added modifying metals such as gallium. More particularly, the only gallium in the catalyst may result from unavoidable trace gallium impurities either in the binder or in the sources of silica and alumina used to prepare the zeolite.

The paraffin conversion process of the present invention may take place either in a fixed bed or a fluid bed of catalyst particles. Particularly, when a fluid bed process is used, the process parameters may be adjusted to cause partial deactivation of the catalyst, thereby enabling the increase in selectivity to $C_6$–$C_8$ aromatics and $C_2$–$C_4$ olefins. In such a fluid bed process, the paraffinic feedstock is contacted with a fluid bed of catalyst, whereby conversion products are generated. Lighter hydrocarbons can be separated from the catalyst by conventional techniques such as cyclone separation and, possibly, steam stripping. However, the dense hydrocarbonaceous deposit (e.g. coke) which forms on the catalyst is more difficult to remove. This hydrocarbonaceous deposit may be removed by transporting the catalyst to a separate regenerator reactor, wherein the hydrocarbonaceous deposit is burned off the catalyst. The regenerated catalyst may then be returned to the fluid bed reactor for further contact with the paraffinic feedstock.

EXAMPLES

A mixture of $C_5$–$C_{10}$ aliphatic hydrocarbons rejected from the Udex extraction of refinery light reformate (Udex raffinate) was converted over a fluid bed catalyst incorporating 25 wt. % of a ZSM-5 zeolite. The catalyst composites had an alpha activity of 18 as measured by the standard n-hexane cracking cited above. Example 1 was carried out at approximately 1150° F., 0.5 WHSV raffinate (based on total catalyst weight) and atmospheric pressure. Example 2 shows the beneficial effects of adding 0.2 WHSV propane which effects include increased $C_2$–$C_4$ olefin yield, as well as reduced coke make. The results of Examples 1 and 2 are presented in Table 3.

TABLE 2

| UDEX Raffinate Composition | |
|---|---|
| Component | Wt. % |
| $C_4$ paraffins | 0.09 |
| $C_5$ paraffins | 3.87 |
| $C_5$ olefins and naphthenes | 0.87 |
| $C_6$ paraffins | 51.44 |
| $C_6$ olefins and naphthenes | 3.06 |
| $C_7$ paraffins | 32.33 |
| $C_7$ olefins and naphrhenes | 0.31 |
| $C_8+$ PON | 3.80 |
| Benzene | 0.16 |
| Toluene | 3.98 |
| Xylenes | 0.09 |
| Other Properties: | |
| Specific gravity: | 0.674 |
| Clear (R + O) octane number: | 66.5 |

TABLE 3

Effect of propane cofeed: 1150° F., 0.5 raffinate WHSV, 1–2 psig, 18 steamed HZSM-5.

| | Example 1 Raffinate Only | Example 2 Raffinate + Propane Co-Feed |
|---|---|---|
| WHSV Propane | 0 | 0.2 |
| Net Yield, Wt. % PON | | |
| Hydrogen | 1.8 | 1.9 |
| Methane | 9.8 | 12.2 |
| Ethane | 7.7 | 8.3 |

TABLE 3-continued

Effect of propane cofeed: 1150° F., 0.5 raffinate WHSV, 1-2 psig, 18 steamed HZSM-5.

| | Example 1 Raffinate Only | Example 2 Raffinate + Propane Co-Feed |
|---|---|---|
| Ethene | 15.9 | 21.1 |
| Propene | 16.2 | 21.7 |
| Butenes | 5.2 | 7.3 |
| Propane | 7.4 | 4.8 |
| Butanes | 1.9 | 2.0 |
| Benzene | 12.2 | 9.4 |
| Toluene | 10.6 | 7.9 |
| EB | 0.7 | 0.1 |
| Xylenes | 4.5 | 4.0 |
| $C_9+$ Ar. | 1.6 | 1.0 |
| Relative Coke yield, wt. % raffinate | 1.0 | 0.6 |

Changes and modifications in the specificity described embodiments can be carried out without departing from the scope of the invention which is intended to be limited only by the scope of the appended claims.

What is claimed is:

1. A process for converting a paraffinic feedstream containing at least 76 weight percent $C_6$–$C_7$ paraffins comprising the steps of:
    (a) charging said paraffinic feedstream to a reaction zone containing a composite catalyst comprising a zeolite having a Constraint Index of between 1 and about 12 and Alpha Value of between 5 and 30 together with a supplemental feedstream containing at least 85 weight percent propane under conversion conditions including temperature of from about 400° C. to about 700° C., pressure of from about 0.1 atmosphere to about 60 atmospheres and weight hourly space velocity from about 0.1 to about 400;
    (b) controlling the mass flowrate of said supplemental feedstream to maintain a weight ration of $C_6$–$C_7$ paraffins to propane of between about 2:1 and 3:1 to enhance the extent of conversion of said paraffinic feedstream to $C_2$–$C_4$ olefins; and
    (c) recovering a product having more than 40 weight percent $C_2$–$C_4$ olefins and more than 10 weight percent $C_6+$ aromatics.

2. The process of claim 1 wherein said zeolite has the structure of at least one selected from the group consisting of ZSM-5, ZSM-11, ZSM-22, ZSM-23, ZSM-35 and ZSM-48.

3. The process of claim 2 wherein said zeolite has the structure of ZSM-5.

4. The process of claim 1 wherein said paraffinic feedstream is a raffinate from a solvent extraction treatment which removes aromatics from a hydrocarbon stream.

5. The process of claim 4 wherein said paraffinic feedstream is a Udex raffinate.

6. The process of claim 5 wherein said supplemental feedstream consists essentially of propane.

7. A method for improving the yield of $C_2$–$C_4$ olefins and decreasing the production of coke derived from catalytic conversion of a paraffinic feedstream containing at least 76 weight percent $C_6$–$C_7$ paraffins comprising the steps of:
    (a) contacting said paraffinic feedstream and a second feedstream containing at least 85 weight percent propane with a composite catalyst containing a zeolite having a Constraint Index of between about 1 and about 12 and Alpha Value of between 5 and 30 under conversion conditions including temperature of from about 400° C. to about 700° C., pressure of from about 0.1 atmosphere to 60 atmospheres and weight hourly space velocity from about 0.1 to about 400;
    (b) controlling the mass flowrate of said supplemental feedstream to maintain a weight ration of $C_6$–$C_7$ paraffins to propane of between about 2:1 and 3:1 to enhance conversion of said paraffinic feedstream to $C_2$–$C_4$ olefins;
    (c) recovering a product having more than 40 weight percent $C_2$–$C_4$ olefins and more than 10 weight percent $C_6+$ aromatics; and
    (d) limiting coke production to less than 1.0 weight percent of the product stream.

8. The process of claim 7 wherein said zeolite has the structure of at least one selected from the group consisting of ZSM-5, ZSM-11, ZSM-22, ZSM-23, ZSM-35 and ZSM-48.

9. The process of claim 8 wherein said zeolite has the structure of ZSM-5.

10. The process of claim 7 wherein said paraffinic feedstream is a raffinate from a solvent extraction treatment which removes aromatics from a hydrocarbon stream.

11. The process of claim 10 wherein said supplemental feedstream consists essentially of propane.

12. The process of claim 11 wherein said paraffinic feedstream is a Udex raffinate.

13. A method for prolonging the useful life of a composite catalyst containing a zeolite in the conversion of a paraffinic feedstream containing at least 76 weight percent $C_6$–$C_7$ paraffins which conversion process comprises contacting said paraffinic feedstream with said composite catalyst containing a zeolite having a Constraint Index of between about 1 and about 12 under conversion conditions including temperature of from about 400° C. to about 700° C., pressure of from about 0.1 atmosphere to 60 atmospheres and weight hourly space velocity based on said paraffinic feedstream, said method for prolonging the useful life of said zeolite catalyst comprising cofeeding with said paraffinic feedstream a supplemental feedstream containing at least 85 weight percent propane at a flowrate sufficient to maintain a weight ratio of $C_6$–$C_7$ paraffins to propane of between about 2:1 and 3:1 to shift the product distribution attributable to conversion of said paraffinic feedstream to increase $C_2$–$C_4$ olefin yield, evolving a total product stream having more than 40 weight percent $C_2$–$C_4$ olefins and more than 10 weight percent $C_6+$ aromatics, whereby the aging rate of said composite catalyst is reduced and the useful life of said composite catalyst is prolonged.

14. The process of claim 13 wherein said zeolite has the structure of at least one selected from the group consisting of ZSM-5, ZSM-11, ZSM-22, ZSM-23, ZSM-35 and ZSM-48.

15. The process of claim 14 wherein said zeolite has the structure of ZSM-5.

16. The process of claim 13 wherein said paraffinic feedstream is a raffinate from a solvent extraction treatment which removes aromatics from a hydrocarbon stream.

17. The process of claim 13 wherein said paraffinic feedstream is a Udex raffinate.

18. The process of claim 17 wherein said supplemental feedstream consists essentially of propane.

* * * * *